(12) United States Patent
Whitfill et al.

(10) Patent No.: US 11,041,217 B2
(45) Date of Patent: Jun. 22, 2021

(54) **AUXOTROPHIC STRAINS OF *STAPHYLOCOCCUS* BACTERIUM**

(71) Applicant: Azitra Inc, Farmington, CT (US)

(72) Inventors: Travis Michael Whitfill, Dallas, TX (US); Ming-De Deng, Manitowoc, WI (US); David Richard Dodds, Manlius, NY (US); Alexander Tikhonov, Branford, CT (US)

(73) Assignee: Azitra Inc, Branford, CT (US)

( * ) Notice: Subject to any disclaimer, the term of this patent is extended or adjusted under 35 U.S.C. 154(b) by 7 days.

(21) Appl. No.: 16/239,871

(22) Filed: Jan. 4, 2019

(65) Prior Publication Data

US 2019/0256935 A1    Aug. 22, 2019

Related U.S. Application Data

(60) Provisional application No. 62/614,096, filed on Jan. 5, 2018.

(51) Int. Cl.
*C12R 1/45* (2006.01)
*C12N 15/74* (2006.01)
*C12N 15/10* (2006.01)
*C12N 1/20* (2006.01)
*C12N 9/10* (2006.01)
*C12N 9/90* (2006.01)
*C12N 15/00* (2006.01)

(52) U.S. Cl.
CPC .................. *C12R 1/45* (2013.01); *C12N 1/20* (2013.01); *C12N 9/1096* (2013.01); *C12N 9/90* (2013.01); *C12N 15/00* (2013.01); *C12N 15/102* (2013.01); *C12N 15/74* (2013.01); *C12Y 206/01021* (2013.01); *C12Y 501/01001* (2013.01); *C12N 2320/10* (2013.01); *C12N 2510/00* (2013.01)

(58) Field of Classification Search
None
See application file for complete search history.

(56) References Cited

U.S. PATENT DOCUMENTS

| | | |
|---|---|---|
| 2010/0150956 A1 | 6/2010 | Patti et al. |
| 2011/0262477 A1 | 10/2011 | Cheng et al. |
| 2016/0235834 A1 | 8/2016 | Bou Arevalo et al. |

OTHER PUBLICATIONS

Moscoso et al.,"A D-Alanine auxotrophic live vaccine is effective against lethal infection caused by *Staphylococcus aureus*", Virulence 9(1): 604-620, Jan. 1, 2018. (Year: 2018).*

Cabral et al.."Design of live attenuated bacterial vaccines based on D-glutamate auxotrophy", Nat. Commun. 8, 15480 doi: 10.1038/ncomms 15480 (2017). (Year: 2017).*

Wei et al., Alanine racemase is essential for the growth and interspecies competitiveness of Streptococcus mutans. Int J Oral Sci. Dec. 16, 2016;8(4):231-238.

Zhang et al., Inactivation of glutamate racemase (MurI) eliminates virulence in Streptococcus mutans. Microbiol Res. May-Jun. 2016;186-187:1-8.

International Search Report and Written Opinion for Application No. PCT/US2019/012287, dated Jun. 14, 2019, 14 pages.

* cited by examiner

*Primary Examiner* — Anand U Desai

(74) *Attorney, Agent, or Firm* — McCarter & English, LLP; Jonathan M. Sparks

(57) ABSTRACT

The present disclosure provides recombinant *Staphylococcus* bacterium (e.g. *S. epidermidis*) that are dependent on D-alanine for growth. In one aspect, the disclosure features a recombinant *Staphylococcus* bacterium comprising two inactivated alanine racemase genes (Δalr1Δalr2); and an inactivated D-alanine aminotransferase (dat) gene. In another aspect, the disclosure features a method of making the recombinant *Staphylococcus* bacterium.

12 Claims, 6 Drawing Sheets

Specification includes a Sequence Listing.

AUXOTROPHIC STRAINS OF *STAPHYLOCOCCUS* BACTERIUM

RELATED APPLICATIONS

This application claims priority to U.S. Provisional Patent Application No. 62/614,096, filed on Jan. 5, 2018, the entire contents of which is incorporated herein by reference in its entirety for all purposes.

The instant application contains a Sequence Listing which has been submitted electronically in ASCII format and is hereby incorporated by reference in its entirety. Said ASCII copy, created on Feb. 7, 2019, is named 129062-00320_SL.txt and is 2,974 bytes in size.

BACKGROUND OF THE INVENTION

Many bacteria utilize the two amino acids D-alanine and D-glutamic acid in the biosynthesis of the peptidoglycan layer, which is necessary for the construction of a functional cell wall in such bacteria. Gram positive bacteria, including species in the *Staphylococcus* genus, utilize D-alanine and D-glutamic acid for the synthesis of the peptidoglycan layer in their cell walls.

The genetic codes provides codons for 20 proteogenic amino acids, 19 of which possess chirality and are the L-isomer. These are considered the "natural" or "standard" amino acids. Amino acids possessing opposite chirality, that is, the D-isomer, are considered non-natural, and are not generally present in the environment. If an organism, such as a bacteria, requires a D-amino acid, then an enzyme or enzymes to produce such non-natural amino acids must be present in the bacteria, or must be deliberately provided to the bacteria, or it cannot survive.

Alanine racemase is an enzyme that catalyzes the conversion of L-alanine to D-alanine, a key building block in the biosynthesis of the peptidoglycan layer in bacterial cell walls. Alanine racemases are typically absent in eukaryotes but ubiquitous among prokaryotes.

Since D-alanine is essential for bacterial cell wall formation and thus for survival of the bacteria, bacteria have an enzyme which can catalyze the production of D-alanine. As D-alanine is very important to the existence of the bacteria, it may possess redundant or multiple enzymes for D-alanine biosynthesis. For example, bacteria may contain multiple alanine racemase genes. In species with two genes, one may be constitutively expressed and anabolic, while the other is inducible and catabolic (Strych, U. et al. 2007. BMC Microbiol. 7:40; Strych U. et al., Curr. Microbiol. 41:290-294; Strych U. et al., FEMS Microbiol. Lett. 196:93-98). These genes supply the D-alanine needed for cell wall biosynthesis, and knockout studies with several of these bacteria have established that the alanine racemase enzyme is essential for growth in the absence of exogenous D-alanine (Franklin, F. C., and W. A. Venables. 1976. Mol. Gen. Genet. 149:229-237; Hols, P., et al. J. Bacteriol. 179:3804-3807; Palumbo, E., et al. FEMS Microbiol. Lett. 233:131-138; Steen, A., et al. J. Bacteriol. 187:114-124; Wijsman, H. J. 1972. Genet. Res. 20:269-277).

Removing the ability of a micro-organism to produce an amino acid that is necessary for growth produces a micro-organism known as an auxotroph. The amino acid that is necessary for growth must be provided exogenously if survival and growth of the micro-organism is desired. Creation of auxotrophic micro-organisms is well known, especially for *E. coli*. (publically available on the world wide web at cgsc2.biology.yale.edu/Auxotrophs.php; Methods Enzymol. 2015; 565:45-66. doi: 10.1016/bs.mie.2015.05.012. Epub 2015 Jun. 10. "*Escherichia coli* auxotroph host strains for amino acid-selective isotope labeling of recombinant proteins." Lin M T, Fukazawa R, Miyajima-Nakano Y, Matsushita S, Choi S K, Iwasaki T, Gennis R B; Nicola Casali, Methods in Molecular Biology, Vol 235. www.springer.com/gp/book/9781588291516, the contents of each being incorporated by reference in its entirety herein).

D-alanine auxotrophs of *Staphylococcus aureus* have been produced for the purpose of producing vaccines against methicillin resistant strains of *Staphylococcus aureus*. (Moscoso M, et al. 27th ECCMID 22-25 Apr. 2017, The Congress of ESCMID (P0473); Moscoso et al., Virulence (2018) Vol. 9(1): 604-620, the contents of each being incorporated by reference in its entirety herein). In this case, it was found necessary to not only knockout the two alanine racemases alr1 and alr2, but also a third enzyme.

If a bacteria is to be introduced into a target environment, it is desirable to be able to control the introduced bacteria after introduction into the target environment, for example, to control the growth of the introduced bacteria relative to the growth of bacterial populations already present in the target environment.

Such control can be imposed by the use of antibiotics, which are selectively toxic to the bacteria being introduced, but which are not toxic to the bacterial populations present in the target environment. However, it is frequently not possible to find antibiotics that have such selectivity. Further, it is frequently undesirable to use antibiotics as these can perturb the target environment in an undesirable manner, for example, the induction of antibiotic resistance in members of the existing bacterial population, or perturbation of the target environment resulting in dysbiosis, or an undesirable situation, for example, diarrhea.

Thus, it is advantageous to use a method of selectively controlling the growth of a bacteria that is to be introduced into a target environment, that does not depend on the use of antibiotics. Introducing auxotrophy into the bacteria to be introduced into the target environment would allow such desired control. This is especially advantageous for the purpose of introducing bacteria into a target environment for the purpose of augmenting or otherwise altering the microbiome of the target environment, and most especially when the target environment is the human microbiome.

The gram-positive bacteria *Staphylococcus epidermidis* is a known member of the human microbiome (Zhang et al, Molecular Microbiology (2003) 49(6), 1577-1593, "Genome-based analysis of virulence genes in a non-biofilm-forming *Staphylococcus epidermidis* strain (ATCC 12228)", incorporated by reference in its entirety herein). *S. epidermidis* is a facultative anaerobic bacteria, and is part of the normal human flora. Although *S. epidermidis* is not usually pathogenic, patients with compromised immune systems are at risk of developing infection. These infections are generally hospital-acquired (Levinson, W. (2010). Review of Medical Microbiology and Immunology (11th ed.). pp. 94-99, incorporated by reference in its entirety herein). *S. epidermidis* is a particular concern for people with catheters or other surgical implants because it is known to form biofilms that grow on these devices.

The present disclosure therefore addresses the need for *Staphylococcus* bacterium (e.g. *S. epidermidis*) that is auxotrophic, and dependent on exogenously supplied nutrients such D-alanine or D-glutamic acid for survival and growth.

SUMMARY OF THE INVENTION

The disclosure relates generally to recombinant *Staphylococcus* bacterium (e.g. *S. epidermidis*) that are dependent on D-alanine for growth. It is a finding of the present disclosure that the growth of a bacteria (e.g. a recombinant *Staphylococcus* bacterium (e.g. *S. epidermidis*)) in a target environment can be selectively controlled without the use of antibiotics. According to some embodiments of the disclosure, the characteristic of auxotrophy is useful for maintaining the presence of a plasmid that does not require the presence of a gene for antibiotic resistance. Thus, in some embodiments, the recombinant *Staphylococcus* bacterium does not comprise a gene for antibiotic resistance. In some embodiments, a polynucleotide allowing the expression of an enzyme or other component that returns the ability of metabolically producing the exogenous nutrient is incorporated in the plasmid that is desired to be maintained in the micro-organism. In some embodiments, the recombinant *Staphylococcus* bacterium is transformed with a pUBTR114-based vector. In further embodiments, the pUBTR114-based vector is pUBTR119*-Sal-GFP.

In one aspect, the disclosure features a recombinant *Staphylococcus* bacterium comprising two inactivated alanine racemase genes (Δalr1Δalr2); and an inactivated D-alanine aminotransferase (dat) gene. In some embodiments, the *Staphylococcus* bacterium is dependent on D-alanine for growth. In another embodiment, the *Staphylococcus* bacterium is *Staphylococcus epidermidis* (*S. epidermidis*), and subspecies thereof. In one embodiment, the *Staphylococcus* bacterium further comprises one or more additional mutations. In some embodiments, the additional mutation comprises an inactivated glutamatic acid racemase gene, MurI. In some embodiments, the *Staphylococcus* bacterium further comprises a polynucleotide encoding a protein with therapeutic properties (e.g., a soluble therapeutic protein). In some embodiments, the protein with therapeutic properties exhibits enzymatic or biological activity. In some embodiments, the protein is a growth factor. In some embodiments, the protein is a hormone.

In another aspect, the disclosure features a method of making a recombinant *Staphylococcus* bacterium comprising (i) transforming a plasmid comprising D-alanine aminotransferase (dat) knockout into competent cells of *Staphylococcus* strain (SEΔalr1Δalr2); (ii) detecting the presence of the knockout plasmid in transformed cells; (iii) incubating the transformed cells identified in step (ii); and (iv) purifying isolated colonies. In some embodiments, the method further comprises testing the isolated colonies for D-alanine auxotrophy. In some embodiments, the presence of knockout plasmid in transformants is detected using Polymerase Chain Reaction (PCR). In some embodiments, recombinant *Staphylococcus* bacterium is *Staphylococcus epidermidis* (*S. Epidermidis*), and subspecies thereof. In some embodiments, the method further comprises transforming the recombinant *Staphylococcus* bacterium with a pUBTR114-based vector. In some embodiments, the pUBTR114-based vector is pUBTR119*-Sal-GFP. In some embodiments, the recombinant *Staphylococcus* bacterium is produced by the foregoing methods.

In another aspect, the disclosure features a kit comprising the recombinant *Staphylococcus* bacterium of any one of the aspects or embodiments described herein. In some embodiments, the kit further comprises a pUBTR114-based vector.

BRIEF DESCRIPTION OF THE DRAWINGS

In FIG. 2A, PCR was performed using primers 1423-5F and 1423-3R to distinguish wild type SE1423 locus (PCR product of 2.3 Kb) and SE1423 knockout (PCR product of 1.5 Kb). In FIG. 2B, PCR was performed using primers 1423-F and 1423-R to detect a PCR product of 0.7 Kb, specific for the wild type SE1423 locus. As expected the PCR product was not generated from the SE1423 knockout plasmid and putative SE1423 knockout SE clones. Results confirmed successful SE1423 deletion in Clones #7, #12 and #18.

DETAILED DESCRIPTION OF THE INVENTION

I. Definitions

Figure 1:
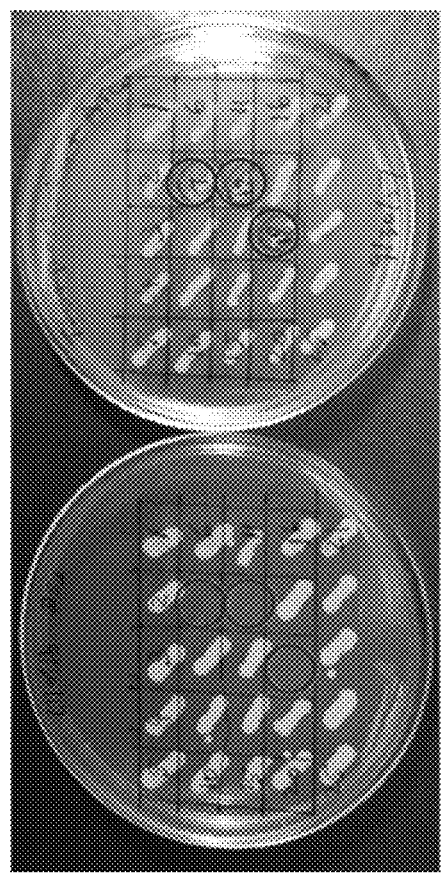
FIG. 1 shows the observation of D-alanine auxotrophy in *S. epidermidis* strains with triple genes knockout (SEΔalr1Δalr2Δdat). Following transformation with SE1423 knockout plasmid, plasmid integration and removal of the plasmid backbone, cells were plated for colonies. Twenty-five colonies were patched onto two different plates, and the plates were incubated at 30° C. overnight. Left: TSA plate; Right: TSA+Anhydrotetracycline (2 µg/mL)+D-alanine (40 µg/mL). Three clones (#7, #12 and #18, indicated in a circle) could only grow on TSA supplemented with D-alanine.

Unless defined otherwise, all technical and scientific terms used herein have the meaning commonly understood by a person skilled in the art to which this invention belongs.

The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The articles "a" and "an" are used herein to refer to one or to more than one (i.e. to at least one) of the grammatical object of the article. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

As used herein, the term "auxotrophic" or "auxotrophy" refers to inability of an organism to synthesize a particular compound required for its growth. An auxotroph is an organism that displays this characteristic.

As used herein, the term "alrA" and "alr" refer to the D-alanine racemase gene, including normal alleles of the alrA gene. In some embodiments, the alr gene from *S. epidermidis* (UniProtKB-Q8CNK7 (ALR_STAES) encodes a D-alanine racemase protein (EC 5.1.1.1). In some embodiments, the locus identifiers SE1674 (alr1) and SE1079 (alr2) refer to specific *S. epidermidis* D-alanine racemase genes.

As used herein, the term "dat" refers to the D-alanine aminotransferase gene, including normal alleles of the dat gene. In some embodiments, the dat gene from *S. epidermidis* (UniProtKB-Q8CS41 (DAAA_STAES)) encodes a D-alanine aminotransferase protein (EC:2.6.1.21). In some embodiments, the locus identifier SE1423 (dat) refers to a specific *S. epidermidis* D-alanine aminotransferase gene. As used herein, the term "murI" refers to the glutamate racemase gene, including normal alleles of the murI gene. In some embodiments, the murI gene from *S. epidermidis* (UniProtKB-Q8CPL0 (MURI_STAES)) encodes a glutamate racemase protein (EC:5.1.1.3). In some embodiments, the locus identifier SE0843 (murI) refers to a specific *S. epidermidis* glutamate racemase gene.

As used here, the term "genetic element" is meant to refer to a polynucleotide comprising a region that encodes a polypeptide or a polynucleotide region that regulates replication, transcription or translation or other processes important to expression of the polypeptide in a host cell, or a polynucleotide comprising both a region that encodes a polypeptide and a region operably linked thereto that regulates expression. Genetic elements may be comprised within a vector that replicates as an episomal element; that is, as a molecule physically independent of the host cell genome. They may be comprised within plasmids. Genetic elements also may be comprised within a host cell genome; not in their natural state but, rather, following manipulation such as isolation, cloning and introduction into a host cell in the form of purified DNA or in a vector, among others.

As used herein, the term "host cell" is meant to refer to a cell which has been transformed or transfected, or is capable of transformation or transfection by an exogenous polynucleotide sequence.

The term "isolated" for the purposes of the present invention designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated."

An "isolated nucleic acid molecule" (such as, for example, an isolated promoter) is one which is separated from other nucleic acid molecules which are present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule in the genomic DNA of the organism from which the nucleic acid molecule is derived.

As used herein, the term "knockout" refers to the disabling of the useful expression of a gene product (for example, and enzyme) by entire or partial removal of a gene, the partial or entire removal of the non-coding control regions necessary for useful expression of the gene product, the insertion of nucleotides into the polynucleotide encoding the gene, or other method for the prevention of useful expression of a gene product.

As used herein, the terms "polypeptide" or "protein" refer to biological molecules, or macromolecules composed of amino-acid residues bonding together in a chain. The definition of polypeptides used herein is intended to encompass proteins (generally higher molecular weight) composed of one or more long chains of amino acid residues and small peptides (generally lower molecular weight) of a few amino acids. In other embodiments, a single amino acid, although not technically a polypeptide, is also considered within the scope of the invention.

As used herein, a "promoter" is meant to refer to a DNA sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. For example, a promoter may be regulated in a tissue-specific manner such that it is only active in transcribing the associated coding region in a specific tissue type(s).

As used herein, the term "polynucleotide(s)" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. The term polynucleotide also embraces short polynucleotides often referred to as oligonucleotide(s). "Polynucleotide" and "nucleic acid" are often used interchangeably herein.

As used herein, the term "therapeutic protein" is meant to refer to a protein, peptide, glycoprotein or glycopeptide that is administered to a subject to treat disease or dysfunction or to improve health of the subject. In some embodiments, the subject is a human. In some embodiments, the therapeutic protein is a human protein. Using the methods disclosed herein, the therapeutic protein is produced in a *Staphylococcus* bacteria, such as for example, *Staphylococcus epidermidis*, that is genetically altered to have a double alanine racemase genes (e.g., alr1 and alr2) knockout and an alanine aminotransferase gene (dat, SE1423) knockout.

II. Compositions

The present disclosure describes a triple knockout *Staphylococcus* bacteria that is a D-alanine auxotroph. The present disclosure provides engineered *Staphylococcus* bacteria, such as for example, *Staphylococcus epidermidis*, that are genetically altered to have a double alanine racemase genes (e.g., alr1 and alr2) knockout and an alanine aminotransferase gene (dat, SE1423) knockout. The present disclosure provides triple knockout *S. epidermidis* strains (SEΔalr1Δalr2Δdat) that have the desired D-alanine auxotrophy.

D-Alanine is an essential component for bacteria with a peptidoglycan layer structure. The essentiality of D-alanine stems from the key role of the dipeptide D-alanyl-D-alanine in the cross-linking of peptidoglycan strands. As described in the present disclosure, double alanine racemase genes knockout *S. epidermidis* strains (SEΔalr1Δalr2) were previously developed. However, the double knockout strains did not exhibit D-alanine auxotrophy, in contrast to *Bacillus subtilis, Escherichia coli* and some other bacteria species. It was believed that the presence of glutamate racemase (interconverting L-glutamate and D-glutamate) and D-alanine aminotransferase (interconverting D-alanine and D-glutamate) in *S. epidermidis* could provide a bypass for alanine racemase. Therefore, the present disclosure provides a knockout of the alanine aminotransferase gene (dat, SE1423) in the double knockout strain (SEΔalr1Δalr2) that shows D-alanine auxotrophy.

The present disclosure provides bacterial host cells genetically engineered to have a deletion in a dat gene, or homolog thereof, such that the activity of D-alanine aminotransferase is reduced, thereby rendering the cell as a D-alanine auxotroph. In some embodiments, a bacterial cell is genetically engineered to comprise a deletion in another gene or operon, which influences the dat operon such that the activity of D-alanine aminotransferase is reduced, thereby rendering the cell as a D-alanine auxotroph.

In some embodiments, the D-alanine auxotrophic bacteria described herein, e.g. the engineered *Staphylococcus* bacteria, such as for example, the triple knockout *S. epidermidis* strains (SEΔalr1Δalr2Δdat), further comprise auxotrophy for another amino acid, vitamin and/or nucleotide. For example, in some embodiments, the D-alanine auxotrophic bacteria described herein can further comprise auxotrophy for one or more of the following amino acids: Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, and Valine. In some embodiments, the D-alanine auxotrophic bacteria described herein can further comprise auxotrophy for a vitamin, such as vitamin A, vitamin B (e.g. B-1, B-2, B-3, B-4, B-5, B-6, B-7, B-8, B-9, B-10, B-11, B-12), vitamin C, vitamin D, vitamin E and vitamin K. In some embodiments, the D-alanine auxotrophic bacteria described herein can further comprise auxotrophy for a nucleotide.

Bacterial Strains

The present disclosure provides genetically altered microorganisms, e.g., bacteria. It is contemplated that the methods described herein can be carried out in any *Staphylococcus* bacteria cell, by inactivating or knocking out the gene encoding the protein homolog of dat in that cell, or by otherwise inactivating the expression or activity of this protein. Assignment of a strain to the genus *Staphylococcus* requires it to be a Gram-positive coccus that forms clusters, produces catalase, has an appropriate cell wall structure (including peptidoglycan type and teichoic acid presence) and G+C content of DNA in a range of 30-40 mol %. Examples include, but are not limited to, *S. aureus* group, including *S. argentous, S. aureus, S. schweitzeri, S. simiae; S. auricularis* group, including *S. auricularis; S. carnosus* group, including *S. carnosus, S. condimenti, S. massiliensis, S. piscifermentans, S. simulans; S. epidermidis* group, including *S. capitis, S. caprae, S. epidermidis, S. saccharolyticus; S. haemolyticus* group, including *S. devriesei, S. haemolyticus, S. hominis; S. hyicus-intermedius* group, including *S. agnetis, S. chromogenes, S. felis, S. delphini, S. hyicus, S. intermedius, S. lutrae, S. microti, S. muscae, S. pseudintermedius, S. rostri, S. schleiferi; S. lugdunensis* group, including *S. lugdunensis; S. saprophyticus* group, including *S. arlettae, S. cohnii, S. equorum, S. gallinarum, S. kloosii, S. leei, S. nepalensis, S. saprophyticus, S. succinus, S. xylosus; S. sciuri* group, including *S. fleurettii, S. lentus, S. sciuri, S. stepanovicii, S. vitulinus; S. simulans* group; including *S. simulans; S. warneri* group; including *S. pasteuri, S. warneri*. In one embodiment, the *Staphylococcus* bacteria is *Staphylococcus epidermidis*.

Genetic Construct

The present disclosure utilizes standard molecular biology techniques, e.g., those described in (Sambrook et al. 2001). pJB38 (Boss et al., 2013) was used as plasmid backbone of the knockout vector, which is based on pJB38, an allelic exchange *E. coli*-staphylococcal shuttle vector, further comprising additional design features on the plasmid to improve functionality (Bose, J. L., et al. *Applied and environmental microbiology*. 2013; 79(7):2218-2224). Specific primers were designed for making SE1423 knockout (described below in Example 1 as Table 1).

In some embodiments, the plasmid is constructed by cloning overlapping PCR product at the EcoRI-SalI sites in pJB38 using Top10 *E. coli* as cloning host, using standard molecular biology techniques. Clones are then selected and screened by PCR using primers 1423-5F and 1423-3R (Table 1) to detect the PCR product. A clone of correct SE1423 knockout plasmid (pJB-1423KO) is transformed into dam–/dcm– *E. coli* strain Gm2163. Plasmid DNA is isolated from two Gm2163 transformant clones by using Qiagen Midi Prep Kit and checked by restriction digestion with EcoRI and SalI, as above Uses of Recombinant *Staphylococcus* Bacterium In some embodiments, the *Staphylococcus* bacterium described herein (e.g., *S. epidermidis*, that is genetically altered to have a double alanine racemase genes (e.g., alr1 and alr2) knockout and an alanine aminotransferase gene (dat, SE1423) knockout) further comprises a polynucleotide encoding a protein with therapeutic properties. In some embodiments, the protein is a soluble therapeutic protein. A soluble therapeutic protein refers to a therapeutic protein that is soluble in an aqueous solution. In some embodiments, all of the expressed therapeutic protein, most of the expressed therapeutic protein or some portion of the expressed therapeutic protein can be soluble in the *Staphylococcus* bacterium described herein. In some embodiments, the soluble therapeutic protein is an active protein, e.g., has enzymatic activity, or biological activity, such as binding activity to a ligand or receptor, ability to activity an intracellular signal transduction pathway, or ability to elicit an immune response in a mammal, e.g., a human. In some embodiments, the therapeutic protein is glycosylated or otherwise modified in vitro by one or more glycosyltransferases or modified to increase resistance to proteases.

In some embodiments, the *Staphylococcus* bacterium of the invention can be used to as is, or modified to express a therapeutic polypeptide to treat disease. In one example, the *Staphylococcus* bacterium of the invention can be used to treat skin diseases or disorders. In another embodiment, the *Staphylococcus* bacterium of the invention can be modified to express a therapeutic polypeptide or fragment thereof to treat skin diseases or disorders.

Formulations

It will be further apparent that a formulation for use according to the present invention may comprise any pharmaceutically effective amount of a recombinant *Staphylococcus* bacterium, to produce a therapeutically effective amount of a desired polypeptide, for example, at least about 0.01%, about 0.05%, about 0.1%, about 0.2%, about 0.3%, about 0.4%, about 0.5%, about 0.6%, about 0.7%, about 0.8%, about 0.9%, about 1.0%, about. 1.5%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 20.0%, about 25.0%, about 30.0%, about 35.0%, about 40.0%, about 45.0%, about 50.0% or more by weight of the genetically engineered microorganism, e.g., bacteria, the upper limit of which is about 90.0% by weight of the genetically engineered microorganism, e.g., bacteria.

In an alternative embodiment, the formulation for use according to the present invention can comprise, for example, at least about 0.01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to about 5%, or more by weight of a recombinant *Staphylococcus* bacterium.

III. Methods

The disclosure features methods of making a recombinant *Staphylococcus* bacterium comprising (i) transforming a plasmid comprising D-alanine aminotransferase (dat) knockout into competent cells of *Staphylococcus* strain (SEΔalr1Δalr2); (ii) detecting the presence of the knockout plasmid in transformed cells; (iii) incubating the transformed cells identified in step (ii); and (iv) purifying isolated colonies. In preferred embodiments, the presence of knockout plasmid in transformants is detected using Polymerase Chain Reaction (PCR). In certain embodiments, the method further comprises testing the isolated colonies for D-alanine auxotrophy.

IV. Kits

The present invention also provides kits. In one aspect, a kit of the invention comprises (a) a recombinant *Staphylococcus* bacterium of the invention and (b) instructions for use thereof. The compositions of the invention are described supra. In some embodiments, a composition of the invention comprises recombinant *Staphylococcus* bacterium is dependent on D-alanine for growth.

All publications and patent applications cited in this specification are herein incorporated by reference in their entirety for all purposes as if each individual publication or patent application were specifically and individually indicated to be incorporated by reference for all purposes. The publications discussed herein are provided solely for their disclosure prior to the filing date of the present application. Nothing herein is to be construed as an admission that the inventors described herein are not entitled to antedate such disclosure by virtue of prior disclosure or for any other reason.

The present invention is further illustrated by the following examples, which should not be construed as further limiting. The contents of all figures and all references, patents and published patent applications cited throughout this application, as well as the Figures, are expressly incorporated herein by reference in their entirety.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

The disclosure provides in some embodiments the generation of a *Staphylococcus epidermidis* (*S. epidermidis*) expression system whereby expression plasmids can be maintained without the use of antibiotics. The present experiments document an extended effort to develop a D-alanine auxotroph *S. epidermidis* strain. Double alanine racemase genes knockout *S. epidermidis* strains (SEΔalr1Δalr2) were initially created but did not exhibit D-alanine auxotrophy. It was believed that the presence of glutamate racemase (interconverting L-glutamate and D-glutamate) and D-alanine aminotransferase (interconverting D-alanine and D-glutamate) in *S. epidermidis* could provide a bypass for alanine racemase, as reported in *S. aureus* and *Listeria monocytogenes*. Therefore, the present invention describes the knockout of the alanine aminotransferase gene (dat, SE1423) in addition to the double knockout of the alanine racemase genes in the initial strain (SEΔalr1Δalr2), to develop triple knockout *S. epidermidis* strains (SEΔalr1Δalr2Δdat) that exhibit D-alanine auxotrophy.

Example 1: Vector for Deletion of SE1423 (D-Alanine Aminotransferase)

The methods used to make SE1423 knockout (KO) are described briefly as follows. First, a SE1423 KO plasmid was made using pJB38 (Boss et al., 2013).

Primers

Based on genome sequence of *S. epidermidis* strain 12228, oligonucleotide primers were designed for PCR to develop a SE1423 knockout (KO) vector. Primer sequences, their specific uses and PCR product sizes are listed in Table 1 as shown below.

TABLE 1

Primers for SE1423 Knockout

| Primer | Sequence (5' to 3') | Application |
|---|---|---|
| 1423-5F (EcoRI) | atgcgaattcATGAGCGATACTTATTTGAATC | Amplification of 5' flanking region of SE1423 (0.5 Kb) |
| 1423-5R | ctatgcgattgaatatacttttcCTTAGCATCCTCTTCATTAAC | |
| 1423-3F | gttaatgaagaggatgctaaggaAAAGTATATTCAATCGCATAG | Amplification of 3' flanking region of SE1423 (1.0 Kb) |
| 1423-3R (SalI) | agctgtcgacAGCAGCATACCAATGTCAATC | |
| 1423-F | CATACGAAGATCGAGGCTAC | Amplification of a partial SE1423 (0.7 Kb) |
| 1423-R | GTACCAACTTGTCCGTCTTG | |
| JB-Cm-F | TTGATTTAGACAATTGGAAGAG | To amplify part of the chloramphenicol selection marker (0.7 Kb) in pJB38 |
| JB-Cm-R | AAGTACAGTCGGCATTATCTC | |

Overlapping PCR using primers 1423-5F/1423-3R: 1.5 Kb
PCR product from wild type using primers 1423-5F/1423-3R: 2.3 Kb
F: forward primer
R: reverse primer
Added restriction sites for cloning are shown in underlined bold face letters PCR products of 5' and 3' flanking regions were generated, 0.5 Kb and 1.0 Kb, respectively. They were then used as templates in overlapping PCR to generate a large PCR product (1.5 Kb) that encompassed both the 5' and 3' flanking regions. The overlapping PCR product was cloned at the EcoRI-S all sites in pJB38 using Top10 *E. coli* as cloning host. Clones were selected and screened by PCR using primers 1423-5F and 1423-3R to detect the PCR product of 1.5 Kb. Plasmid DNA was also isolated and digested by EcoRI and SalI to detect both fragments of the vector backbone (7.0 Kb) and the insert (1.5 Kb). A clone of correct SE1423 knockout plasmid (pJB-1423KO) was transformed into dam⁻/dcm⁻ *E. coli* strain Gm2163. Plasmid DNA was isolated from two Gm2163 transformant clones by using Qiagen Midi Prep Kit and checked by restriction digestion with EcoRI and SalI, as above.

Example 2. Generation of Triple Knockout Strains (SEΔalr1 Δalr2Δdat)

pJB-1423KO plasmid isolated from Gm2163 was transformed into competent cells of *S. epidermidis* strain (SEΔalr1Δalr2) using plates of TAS+chloramphenicol (10 µg/mL). The presence of the pJB-1423KO plasmid in transformants was confirmed by detecting the PCR product of 1.5 Kb using primers 1423-5F (EcoRI) and 1423-3R (SalI). In all 26 clones tested, PCR product of 1.5 Kb was observed, while a PCR product of 2.3 Kb was observed in a reaction containing cell lysate from the SE host cells. Cells of two confirmed clones were streaked on fresh plates of TSA+Cm (10 µg/mL)+D-alanine (40 µg/mL). Plates were incubated at 43° C. for 24 hr for plasmid integration via homologous recombination. Isolated colonies were streaked again for purification at 43° C. Four isolated colonies were inoculated into 50 mL TSB+D-alanine (40 µg/mL) in a 250-mL baffled shake flask in order to loop out the plasmid backbone via a second round of homologous recombination. The cultures were shaken at 30° C. for 24 hr. An aliquot of 0.5 mL culture was transferred to a flask containing 50 mL fresh medium. Transfer was repeated three times. Cells from the flask were plated on TSA+Anhydrotetracyclne (ATC 2 µg/mL)+D-alanine (DA, 40 µg/mL). After 2 days of incubation at 30° C., about 100-200 colonies were formed on plates plated with 100 µl of culture at $10^{-5}$ dilution. Further analyses of the colonies are described below.

Example 3. Test for D-Alanine Auxotrophy in the Triple Knockout Strains (SEΔalr1Δalr2Δdat)

A total of 25 isolated colonies from the TSA+ATC+DA plates were patched onto TAS plates and onto TAS+ATC+DA plates. Plates were incubated at 30° C. overnight. All clones grew well on the D-alanine supplemented plate (TSA+ATC+DA). As shown in FIG. 1, three clones (#7, #12 and #18) failed to grow on TSA without D-alanine supplementation, indicating D-alanine auxotrophy. The auxotrophic phenotype was observed again when cells from patches on the TSA+ATC+DA plate were patched again on TSA plates. Note that it was expected that some clones from the TSA+ATC+DA plates would retain the wild type SE1423 locus since the second round of homologous recombination could result in the removal of the plasmid backbone without knocking out SE1423.

Figure 2A:
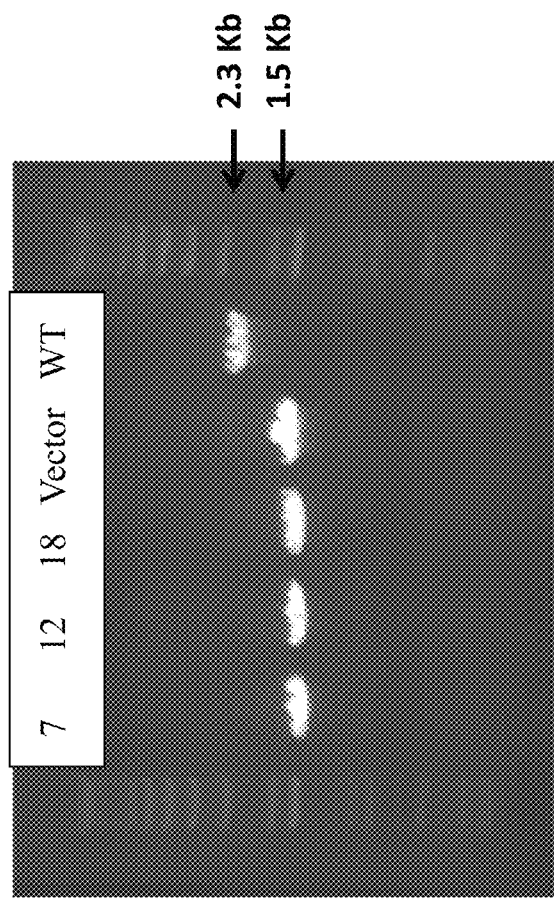
FIG. 2A and FIG. 2B show the results of PCR test of triple knockout strains (SEΔalr1Δalr2Δdat). Cells from patches on a plate of TSA+Anhydrotetracycline (2 µg/mL)+D-alanine (40 µg/mL) were used as template in PCR reactions: Clone #7; KO Clone #12; KO Clone #18; Wild type SE; SE1423KO plasmid DNA (Vector, as control).
Figure 2B:
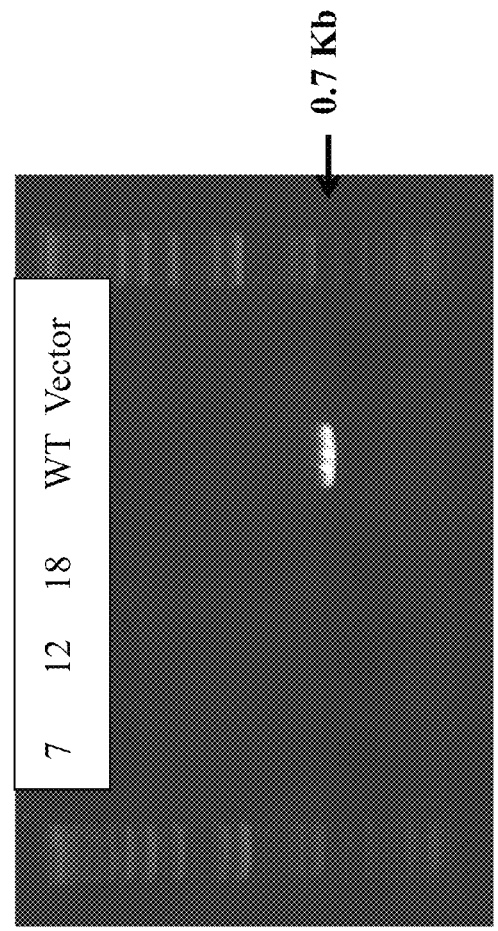

The clones that were D-alanine auxotrophs were further analyzed. When these 1423KO SE clones were patched onto TSA+Cm (10 µg/mL), they did not grow, indicating removal during the second round of homologous recombination of the plasmid backbone including the chloramphenicol selection marker. PCR using primers JB-Cm-F and JB-Cm-R (Table 1) also confirmed the loss of the antibiotic resistance marker (data not shown). PCR using primers 1423-5F and 1423-3R detected a PCR product of 1.5 Kb in these KO clones while the PCR product from the SE host was 2.3 Kb, as expected (FIG. 2A). Wild type SE cells produced a PCR product of 0.7 Kb using primers 1423-F and 1423-R (both specific to SE1423 coding sequence); this PCR product was not detected from the KO plasmid DNA and from the putative KO clones (FIG. 2B).

Therefore, based on all experimental data, it can be concluded that SE1423 (dat, D-alanine aminotransferase) was successfully deleted in the double alanine racemase genes knockout strain, generating a triple knockout S. epidermidis strain (SEΔalr1Δalr2Δdat). Moreover, the desired D-alanine auxotrophy was observed in the triple knockout strain.

D-alanine is required for the synthesis of bacterial cell peptidoglycan. It was enough to delete the alanine racemase gene(s) for D-alanine auxotrophy in B. subtilis and E. coli. However, in order to develop this phenotype in S. epidermidis, two alanine racemase genes (alr1, alr2) and the D-alanine aminotransferase gene dat (SE1423) must be knocked out. Evidently, the combination of glutamate racemase and D-alanine aminotransferase provides a viable bypass to alanine racemase, as reported in S. aureus MRSA132 (Moscoso et al., 2017 and 2018) and Listeria monocytogenes (Thompson et al., 1998). Although the S. epidermidis genome contains a third putative alanine racemase homolog (SE1769), it is not necessary to knock out this gene for D-alanine auxotrophy under the experimental conditions used in this study.

With the successful development of a D-alanine auxotrophic S. epidermidis strain, the next step is to transform the strain using an expression vector that contains an alanine racemase gene as selection marker. Transformants will be selected by plasmid complementation of the D-alanine host auxotrophy.

Example 4. Development of a Staphylococcus epidermidis Expression Vector with a Non-Antibiotic Selection Marker This example describes the development of a Staphylococcus epidermidis expression system whereby expression plasmids can be maintained without the use of antibiotics.

Transformation of Cloning Host Bacillus Subtilis SCK6 with pJB38 pJB38, an E. coli/S. aureus shuttle vector (Bose et al., 2013), is used for protein production in S. epidermidis. One possible approach to develop a non-ABR (antibiotic resistance) protein expression system is to modify pJB38. To explore this option, it was tested if pJB38 could be transformed into cloning host Bacillus subtilis SCK6. pJB38 DNA isolated from E. coli strain DH5a using Qiagen HiSpeed Plasmid Midi Kit reagents and protocol was transformed into SCK6ΔalrA using BTR's protocols for competent cell preparation and transformation (described below). Transformed cells were plated on LB agar+D-alanine (DA, 40 µg/mL)+Chloramphenicol (Cm, 10 µg/mL). Small colonies started to appear after incubation at 30° C. for two days. Colonies were counted after 3 days of incubation at 30° C. When 250 µL of competent cells were transformed with 0.6 µg of pJB38 DNA (in 5 µL), 61 colonies of variable sizes were observed on a plate plated with 50 µL cells. Based on this, transformation efficiency is $5.2 \times 10^2$ cfu/µg DNA.

To confirm the transformants are real, 40 colonies were picked and patched onto a fresh plate of LB agar+DA+Cm and incubated overnight at 30° C. All colonies grew fine. Six clones were each inoculated into 3 mL broth of LB+DA+Cm. Cells were used to prepare mini prep plasmid DNA. Plasmid was digested with EcoRI+HindIII, and SalI+SnaBI. Expected DNA bands from EcoRI+HindIII digestion were 5 Kb and 2 Kb. Bands of SalI+SnaBI digestion were 4.7 Kb and 2.3 Kb. Expected digestion patterns were observed for 3 large-colony clones (#2, #3 and #4) and two small colony clones (#6 and #7). Small-colony clone #5 showed the larger size bands on agarose gels, while the densities of the small bands were very weak. From this data, it could be concluded that pJB38 was successfully transformed into B. subtilis SCK6.

In order to transform pJB38 into S. epidermidis, the plasmid needs to be isolated from a dam⁻/dcm⁻ E. coli host to minimize impact of the host restriction and modification on transformation efficiency. The efforts mainly focused on working with pUBTR114-based vectors.

Transformation of S. epidermidis with Vector pUBTR14-TP

Transformation competent cells of S. epidermidis strain NRRL B-4268 were prepared and transformed. pUBTR114-TP (pUBTR114 vector carrying a test protein gene) was isolated from Bacillus subtilis SCK6 using Qiagen Midi Prep Kit (see Appendix II). Transformed S. epidermidis cells were plated on tryptic soy agar (TSA) plates containing kanamycin at 10 µg/mL. Plates were incubated at 37° C. overnight. From a transformation using ~950 ng plasmid DNA, five colonies were observed. All five colonies regrew at 37° C. after patching onto a fresh kanamycin plate. Cells were picked up using a tooth pick and suspended in 100 µL of Tris buffer (100 mM, pH 8.0). An aliquot of lysate (0.5 µL) was used as template in a 25-µL PCR reaction using Taq Polymerase and primer pair s.p.amyQ-Nde-F2/Sbf-TP-R (Table 2). Cell lysate of untransformed S. epidermidis and plasmid DNA isolated from SCK6 were used as negative and positive controls, respectively. Cell lysates from all five clones generated an expected PCR product of 1.5 Kb. Therefore, these experiments demonstrated that pUBTR114-based vectors can be transformed into and maintained in S. epidermidis using kanamycin selection.

TABLE 2

Primer Sequences

| Name | Sequence (5' to 3') | Application |
|---|---|---|
| s.p. amyQ-Nde-F2 | TTTAcatatgattcagaaacgtaagcggacagatcg | To amplify the TP gene CDS (1.5 Kb) in pUBTR114-TP |
| Sbf-TP-R | TTTTTCTTGGAATTGTGCTGcctgcaggTTAGTGATGGTG | |
| Sar-GFP-F (Paer7I) | acgtctcgagCTGATATTTTTGACTAAACCAAATG | To amplify the expression cassette SarAP1-SsaA-His-sGFP (1.1 Kb) |
| Sar-GFP-R (SbfI) | ctgacctgcaggaGATGATCCGCTACTAACGAC | |

F: forward primer
R: reverse primer
Added restriction sites are shown in underlined bold face letters Construction of pUBTR119-GFP Detectable GFP expression and secretion in *S. epidermidis* transformed with pJB38-sGFP has been demonstrated. Therefore, it was decided to clone the expression cassette "SarAP1-SsaA-His-sGFP" into a pUBTR119-TP for evaluation. This plasmid is similar to pUBTR114-TP. The difference between the two plasmids is the presence of a second promoter sequence and more convenient cloning sites upstream to the TP coding sequence in pUBTR119-TP.

Forward primer Sar-GFP-F and reverse primer Sar-GFP-R (Table 2) were designed to amplify the 1.1-Kb fragment of the sGFP expression cassette by PCR from plasmid pJB38-sGFP. The forward and reverse primers contain restrictions sites PaeR7I and SbfI, respectively. Standard PCR conditions with PfuUltra DNA polymerase from Agilent were used. The PCR product was run through an agarose gel, excised and purified using the Qiagen QIAquick gel extraction kit. The fragment was then digested with PaeR71-SbfI and gel purified one more time. pUBTR119-TP was isolated from *B. subtilis* SCK6 using Qiagen Midi Prep Kit and digested with restriction enzymes PaeR7I and SbfI to remove the 1.5-Kb test protein (TP) coding sequence. The remaining 4.1-Kb vector backbone was gel purified. The sGFP expression cassette was ligated into pUBT119 backbone at the PaeR71-SbfI sites using NEB's Quick Ligation Kit and transformed into *B. subtilis* SCK6ΔalrA competent cells. The transformation mixture was plated onto LB plates as well as LB+10 μg/mL kanamycin+40 μg/mL D-alanine and incubated overnight at 37° C. About 100 colonies were observed on both types of plates, suggesting effective selection by either kanamycin resistance or D-alanine auxotroph complementation. One hundred colonies from the LB plate and 150 colonies from the LB+Kan+DA plate were patched onto plates of LB and LB+Kan+DA, respectively. All showed good growth. Fifteen pools of 10 colonies each from the LB+Kan+DA plate (clones #1-150) and ten pools from the LB plate (#151-250) were screened by PCR using primers Sar-GFP-F/Sar-GFP-R to confirm the presence of the 1.1-Kb insert. Plasmid DNA of pJB38-sGFP and SCK6ΔalrA cells served as positive and negative control. All pools were PCR positive. Individual clones from one pool (Pool #5) were screened by PCR as above and all were positive. These clones from the LB+Kan+DA were grown in liquid LB+KAN+DA at 37° C. overnight. Cells were used for plasmid mini-prep. All ten clones contained the plasmid when checked on agarose gel. Plasmid DNA from clones #3 and #4 were analyzed by three sets of restriction digestions: PaeR71+SbfI, EcoRV, and KpnI. Expected digestion patterns were observed for both clones. Midi prep DNA was made from both clones. Sequencing confirmed successful cloning and did not reveal any mutations. The construct was transformed into SE NRRL B-4268 using kanamycin selection as described above. After a long incubation of 3 days, nine colonies were observed. Two clones were tested by PCR. However, PCR using primers Sar-GFP-F/Sar-GFP-R failed in detecting the sGFP expression cassette.

It is unclear why pUBTR114-TP could be transformed into *S. epidermidis* and confirmed by PCR, while putative transformants from pUBTR119-GFP could not be confirmed. pUBTR114-TP colonies were observed after overnight incubation at 37° C., while pUBTR119-GFP colonies were only observed after 2-3 days of incubation at 37° C. One difference between the two plasmids is the presence of an XhoI restriction site in pUBTR119-GFP. *B. subtilis* possess an XhoI methylation system (Jentsch, 1983). XhoI site in pUBTR119-TP could not be digested by restriction enzyme XhoI, and for this reason, its isoschizomer PaeR71 was used for cloning of the GFP expression cassette. It was suspected that the restriction/modification system in *S. epidermidis* might somehow target pUBTR119-GFP because of methylated XhoI site. Therefore, the vector was modified by replacing the XhoI site with a different restriction site, SalI.

Development of a New GFP Expression Vector: pUBTR119*-SAL-GFP

An overlapping PCR strategy was used to replace the Xho site with a different restriction site (SalI) in pUBTR119-GFP. In this plasmid, there are a MluI-XhoI fragment (840 bp) and an XhoI-KpnI fragment (251 bp). New primers were designed containing nucleotide changes of 5'-CTCGAG-3' to 5'-GTCGAC-3' for PCR amplification of the two fragments and overlapping PCR. The overlapping PCR product (1.1 Kb) was digested with MluI and KpnI, and ligated with pUBTR119-GFP that was predigested with MluI-KpnI. Ligation reaction was transformed into SCK6 competent cells using kanamycin selection as above. A large number of colonies were formed. Colonies were patched onto a fresh plate LB+Kan (10 μg/mL). Twelve clones were analyzed by PCR using primer Mlu-F2 and Sal-R2 (Table 2). Primer Sal-R2 is specific to the SalI site. The band of expected PCR product of 0.84 Kb was weak, but it was clearly present in the reactions for 8 clones. All 12 clones were grown up in liquid medium (LB+Kan) for plasmid DNA mini-preps. All these clones showed a band of the plasmid of correct size and they were linearized by SalI digestion. Clone #4 was grown up for midi prep. DNA was analyzed by restriction digestions: MluI+KpnI; and SalI. As expected, two bands (4.5 Kb and 1.1 Kb) were observed from MluI+KpnI digestion, and SalI linearized the plasmid. The new plasmid is named pUBTR119*-Sal-GFP.

Transformation of *S. epidermidis* Strains with pUBTR119*-SAL-GFP

Figure 3:
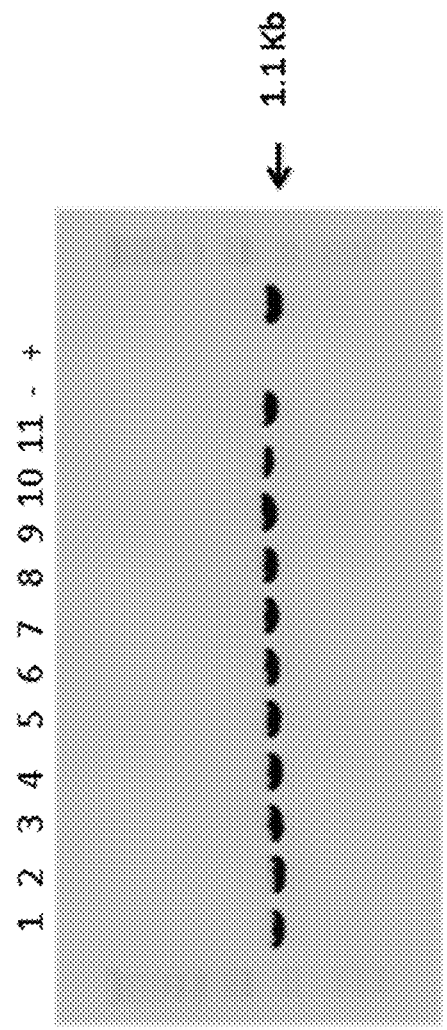
FIG. 3 shows the results of polymerase chain reaction (PCR) of clones of *S. epidermidis* NRRL B-4268 transformed with pUBTR119*-Sal-GFP. Cells of eleven clones (labeled as 1 through 11) were used as templates in PCR reactions using primers Sar-sGFP-F and Sar-sGFP-R to detect a 1.1-Kb PCR product. Cells of SE NRRL B-4268 and plasmid DNA of pUBTR119*-Sal-sGFP isolated from SCK6 served as negative (−) and positive (+) control. All transformant clones were confirmed.

Wild type SE NRRL B-4268 competent cells were transformed with pUBTR119*-Sal-GFP plasmid DNA and plated on plates of TSA+Kan (10 μg/mL). After incubation at 37° C. overnight, two and nine colonies were observed from transformation using ~440 ng and ~880 ng plasmid DNA, respectively. All eleven clones were patched onto a fresh TSA+Kan plate and cells were tested by PCR using primers Sar-GFP-F and Sar-GFP-R. *S. epidermidis* cells and pUBTR119*-Sal-GFP plasmid DNA were used as negative and positive control, respectively. A PCR product of 1.1 Kb was generated in all reactions except the negative control (FIG. 3)

Figure 4:
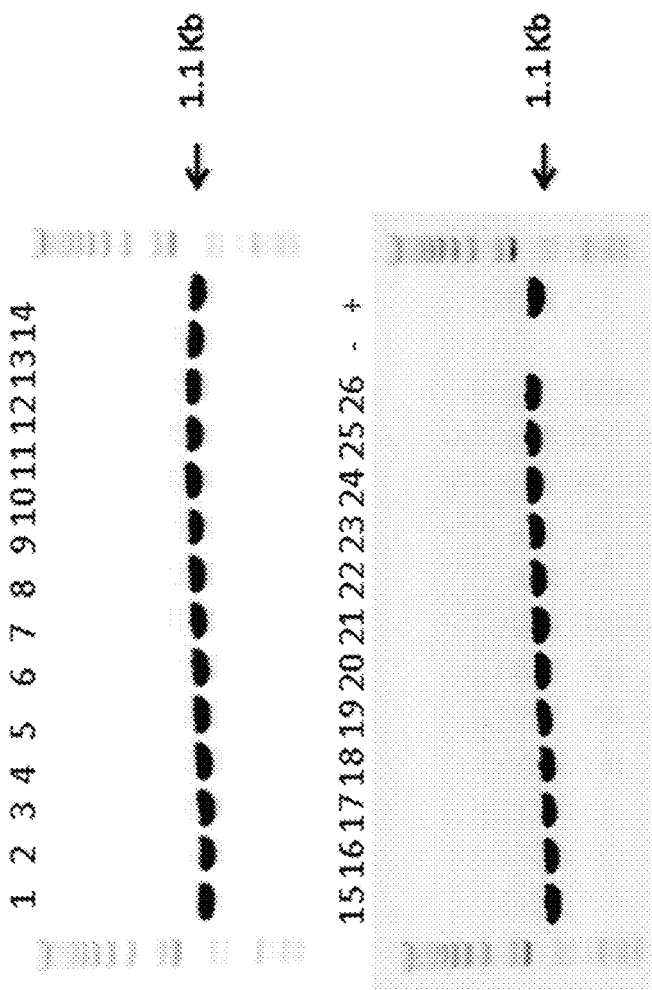
FIG. 4 shows the results of PCR of clones of *S. epidermidis* triple genes knockout strain (SEΔalr1Δalr2Δdat) transformed with pUBTR119*-Sal-GFP by antibiotic selection or D-alanine auxotroph complementation. Cells were used as templates in PCR reactions using primers Sar-sGFP-F and Sar-sGFP-R to detect a 1.1-Kb PCR product. Cells of SE NRRL B-4268 and plasmid DNA of pUBTR119*-Sal-sGFP isolated from SCK6 served as negative (−) and positive (+) control. Clones 1 through 3 were generated from antibiotic selection and Clones 4 through 26 from D-alanine auxotroph complementation. All clones were confirmed.

A D-alanine auxotroph triple knockout strain (SEΔalr1Δalr2Δdat) was grown to prepare transformation competent cells using the same protocol as for NRRL B-4268, except for the addition of D-alanine (40 μg/mL) to the TSB medium. pUBTR119*-Sal-GFP contains both a kanamycin resistance gene and an alanine racemase gene as selection markers. The plasmid was transformed into the triple genes knockout mutant by kanamycin selection on TSA+Kan (10 μg/mL) as well as by D-alanine auxotroph complementation on TSA. Plates were incubated at 37° C. Colonies were observed after overnight incubation: 3 colonies from transformation of 880 ng plasmid DNA on kanamycin selection plates, and 25 colonies on TSA plates from the same amount of plasmid DNA. It appears that *S. epidermidis* transformation using D-alanine auxotroph complementation works more efficiently than using kanamycin selection. All 28 colonies were able to grow after being patched on fresh plates. They were also all confirmed by PCR using primers specific to the gfp gene (FIG. 4).

Cell Cultures for GFP Expression

Figure 5:
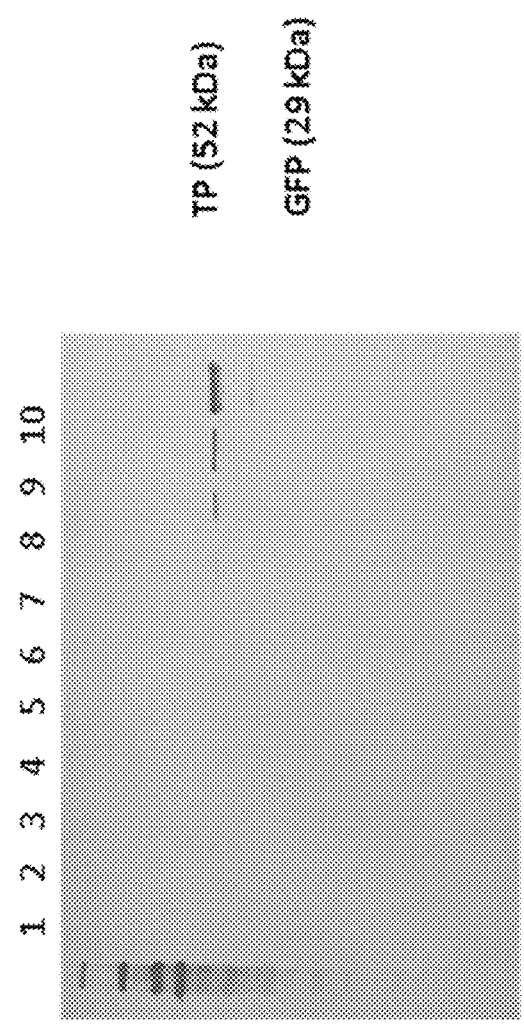
FIG. 5 shows a Western blot for detection of His-tagged protein. Lanes 1 through 6: *S. epidermidis* culture broth samples as listed in Table 2; Lanes 7 through 10: a sample containing a His tagged TP protein (~52 kDa) loaded at dilutions of 1/20, 1/10, 1/5 and 1/1, respectively. No signal for His-tagged GFP protein (29 kDa) was detectable.

A shake flask experiment was set up to evaluate protein expression in the SE triple knockout strain transformed with pUBTR119*Sal-GFP construct. Strains and media used in this experiment are listed in Table 3. A shake flask culture protocol is provided below for growth and protein expression in *B. subtilis* and *S. epidermidis*. Strains were inoculated into 5 mL of the listed medium minus glucose and grown overnight at 37° C., 225 rpm. The overnight culture (0.5 mL) was used to inoculate 50 mL of the listed medium plus 2% glucose in 250-mL baffled flasks. Cultures were grown for 24 hours at 37° C., 225 rpm. All strains showed good growth. Culture broth was collected by centrifuging 1.5 mL of culture for 3 minutes at 13,000 rpm (17,900×g) in an Eppendorf Centrifuge 5417C. FIG. 5 shows a Western blot for detection of His-tagged protein.

TABLE 3

Strains and Culture Media Used in Cell Growth and Protein Expression Experiment

| | Strain | Strain Source | Medium for Flask Culture |
|---|---|---|---|
| 1 | SE WT Host | Proj. 2224A, pos. #4, −80° C. box | TSB + 2% glucose |
| 2 | SEΔalr1Δalr2Δdat #7 Host | Proj. 2224A, pos. #50, −80° C. box | TSB + 40 µg/mL D-alanine + 2% glucose |
| 3 | pUBTR119*Sal-GFP/SEΔalr1Δalr2Δdat #1 | Patch on plate TSA + 10 µg/mL Kan + 40 µg/mL D-alanine | TSB + 10 µg/mL Kan + 40 g/mL D-alanine + 2% glucose |
| 4 | pUBTR119*Sal-GFP/SEΔalr1Δalr2Δdat #1 | Patch on plate TSA + 10 µg/mL Kan + 40 µg/mL D-alanine | TSB + 2% glucose |
| 5 | pUBTR119*Sal-GFP/SEΔalr1Δalr2Δdat #4 | Patch on TSA plate | TSB + 10 µg/mL Kan + 40 g/mL D-alanine + 2% glucose |
| 6 | pUBTR119*Sal-GFP/SEΔalr1Δalr2Δdat #4 | Patch on TSA plate | TSB + 2% glucose |

SDS-PAGE and Western Blot protocols (described below) were followed for detection of GFP with a C-terminal His tag. The secreted His-tagged GFP protein contains 252 amino acid residues and its molecular weight is 29 kDa. A 4-12% protein gel was run and stained, but no protein band of the expected size could be observed (data not shown). Samples were run on a 16% protein gel and transferred onto a membrane for detection using anti-His antibodies. *B. subtilis* SCK6 transformed with pUBTR114-TP was shown previously to express and secret the test protein containing a N-terminal His tag (52 kDa). A culture broth sample saved at −20° C. was loaded as a positive control at various dilutions: 1/1 as the other samples, 1/5, 1/10 and 1/20 fold diluted. The only visible bands observed were from the positive control. Signal was faint in the 1/20-fold diluted control. No signal could be detected for GFP protein on the blot. Therefore, GFP was not actively expressed in these cultures. The medium TSB plus 2% glucose that was experimentally tested to be suitable for protein expression in *B. subtilis*, might not be optimal for protein expression controlled by the SarAP1 promoter, and or protein secretion driven by the signal peptide SsaA.

pUBTR114-based vectors were successfully transformed into *S. epidermidis*. A GFP expression cassette was cloned to construct pUBTR119*-Sal-GFP. The vector contains both a kanamycin resistance gene and an alanine racemase gene as selection markers. The kanamycin gene can be readily removed when desired. pUBTR119*-Sal-GFP was successfully transformed into SE NRRL B-4268 using kanamycin selection. It was also transformed into a triple genes knockout D-alanine auxotroph mutant by kanamycin selection as well as by D-alanine auxotroph complementation. All clones were confirmed by PCR using primers specific to the gfp gene.

These experiments describe the development of a non-antibiotic expression system for protein production in *S. epidermidis*. First, a D-alanine auxotroph *S. epidermidis* strain was developed by successively knocking out two alanine racemase genes (alr1 and alr2) and D-alanine aminotransferase gene (dat). Then, it was validated that the BTR Gram positive bacteria expression vector can be transformed into *S. epidermidis* and complement the host's D-alanine auxotroph. It was found that the expression vector contains replication origin and selection marker functional in both *B. subtilis* and *S. epidermidis*. The highly transformable *B. subtilis* SCK6ΔalrA serves as a cloning host to facilitate vector construction. Once a vector is built and confirmed in *Bacillus*, it is transformed into D-alanine auxotroph *S. epidermidis* strain (SEΔalr1Δalr2Δdat) for protein expression.

The Experiments described above were performed with, but not limited to, the following methods.

Plasmid Preparation from *Bacillus subtilis*

Qiagen QIAprep Spin Miniprep kit was used (cat. #27106) for Mini Preps; Qiagen HiSpeed Plasmid Midi Kit (cat. #12643) was used for Midi Prep. The main point is addition of lysozyme to the P1 Buffer.

Mini Prep:
1. Isolated colonies were inoculated into 5 mL LB+required antibiotic and grown at 37° C., 225 rpm overnight.
2. 3 mL of each overnight culture was removed to a 1.5-mL Eppendorf tube, centrifuged at 13,000 rpm in an Eppendorf Centrifuge 5417C for 1 minute. Supernatant was discarded.
3. The pellets were resuspended in 250 µL P1 Buffer. Lysozyme was added to a final concentration of 200 µg/mL; 5 µL of a fresh 10 mg/mL lysozyme solution in water was added. Samples were vortex'd and incubated at 37° C. for 30 minutes.
4. Follow remaining protocol as instructed in the manufacturer's handbook Preparation of Competent Cells and Transformation of *Bacillus subtilis* Strain SCK6

SCK6 Competent Cell Preparation
1. From a −80° C. glycerol stock vial, streak SCK6 for isolation onto an LB plate. Incubate overnight at 37° C.
2. Inoculate an isolated colony into 5 mL LB in an 18×150 mm glass tube. Shake overnight at 225 rpm at 37° C.
3. Make a 1:100 dilution of the overnight culture to determine $OD_{600}$.
4. Dilute culture to a starting $OD_{600}$ of 1.0 in 15 mL LB+1% xylose in a 125-mL baffled flask. Shake at 225 rpm, 37° C. for 2 hours
5. Freeze down culture @ −80° C. in 10% glycerol: add 3.6 mL of 50% glycerol to the flask and freeze down 450 μL aliquots in 1.5-mL eppendorf tubes at −80° C.

SCK6 has an erythromycin resistance marker on the chromosome. 1.0 μg/mL erythromycin may be added in all steps if desired. For SCK6ΔalrA, D-alanine is added to the medium at 40 μg/mL.

Transformation Protocol
1. Competent cells were thawed at RT, use 200 μL for each transformation.
2. Transforming DNA (plasmid or ligation reaction) was added directly to a 1.5-mL eppendorf tube containing 200 μL competent cells.
3. Eppendorf tubes were put in a 18×150 mm glass tube and placed at 37° C., 225 rpm for 90 minutes.
4. Sample was plated out onto 1-4 LB plates+required antibiotic. Incubate plates at 37° C. overnight.

Growth and Preparation of *Bacillus subtilis* and *S. epidermidis* for Protein Expression Growth Medium: TSB+20 g/L glucose for *Staphylococcus epidermidis* and *Bacillus subtilis* SCK6 wild type hosts and TSB+20 g/L glucose+10 μg/mL kanamycin for transformants of pUBTR114 or pUBTR119 constructs Use −80° C. glycerol scrapings to inoculate 5 mL growth medium listed above for each strain in 18×150 mm glass tubes. Grow overnight at 37° C., 225 rpm Use 0.5 mL overnight culture to inoculate 250-mL baffled flasks containing 50 mL of the same growth medium as above for each strain. Grow for 24 hours at 37° C., 225 rpm Sample flasks by removing 2×1.5-mL aliquots of each 24-hour culture. Centrifuge in Eppendorf Centrifuge 5417C at 13,000 rpm (17,900×g) for 3 minutes. Remove supernatant to a new Eppendorf tube to be used for SDS-PAGE analysis and Anti-His Western Blot. Save the pellets also. All samples saved at −20° C.

Take A600 readings of remaining 24-hour cultures

SDS Page and Western Transfer Protocol for Protein Containing a HIS Tag

Components/Reagents Used: from Expedeon
20× Teo-Tricine-SDS running Buffer #B50500
RunBlue SDS gels 4-12%, 12 well, 10 cm×10 cm #NXG41212
10×DTT Reducer #A32001
4×LDS Sample Buffer #B31010
Invitrogen Novex mini cell XCELL Surelock Electrophoresis Cell
Transfer buffer: 20× Tris-Glycine Blotting Buffer #B86500
BioRad Plus Protein western Standard #161-0376
Genscript One-Hour Western Kit #L00204T
Genscript His-Tag Antibody pAB, Rabbit #A00174; 10 ul aliquots stored at −20C Sample Preparation:
Sample mixture:
X μL Sample
5 μL 4×LDS Sample buffer
2 μL 10×DTT reducing Agent
Y μL Deionized water
Total volume=20
Preparation steps:
Samples are mixed by vortexing
Boiled for 3 minutes
Centrifuged briefly and cooled to RT
Vortex again Set Up and Running of Gels:
Add 40 mL of 20× running buffer to 760 mL of Milli Q $H_2O$
Gels are removed from pouch and rinsed with deionized water. They are then placed in the electrophoresis unit so that the shorter side of the plate is facing in. Once they are locked in place running buffer is added to the inner chamber (approx. 200 mL). Check for leaks before continuing. The remaining running buffer is added to the outer chamber.
Rinse wells with the running buffer
Load the desired amount of prepared sample from above along with 5 μL of the BioRad Western standard
Gels are run at RT, 150 volts for approx. 1 hr (run long enough so that the dye front reaches the bottom of the gel)

Transfer Setup:
Make up 1,000 mL transfer buffer: 50 mL 20× Tris-Glycine Blotting Buffer+200 mL methanol+770 mL $MQH_2O$. Chill buffer to keep transfer cool
Soak sponges in transfer buffer
Equilibrate gel(s) in transfer buffer for 7 min and nitrocellulose (NC) membrane/blotting membrane for 10 min in transfer buffer before setting up sandwich.
Set up sandwich: On a piece of Parafilm set down a piece of pre-soaked Whatman paper. Place the pre-soaked gel on top of the Whatman paper. Put a pre-soaked NC membrane on top of the gel. Using a glass Pasteur pipet, gently roll over the membrane to remove any air bubbles. Place a piece of pre-soaked Whatman paper on top of the NC membrane. Again gently roll over the top to remove air bubbles. Pick up the sandwich and place on top of 2 sponges (that have been squeezed to remove all the transfer buffer) sitting in the blot module. If running only one gel, fill the remaining blot module with squeezed sponges so that they stick approx. 0.5 cm above the unit. If running two gels, place one squeezed sponge on top of the first sandwich. Set up the $2^{nd}$ sandwich exactly as above. Place this on top of the sponge. Fill the remaining blot module with sponges as above.
Use enough transfer buffer to cover the gel/membrane sandwich in the blot module. Use approx. 550 mL $MQH_2O$ in the outer buffer chamber.
Run at room temp, 30 volts for 90 min Western Blots:
GenScript One-Hour Western Kit protocol; signal development with TMB substrate.
10 μL anti-His Ab+100 μL WB-1; use 50 μL/gel

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES

Bose J L et al., 2013. Genetic tools to enhance the study of gene function and regulation in *Staphylococcus aureus*. Applied and Environmental Microbiology 79:2218-2224.

Jentsch S. 1983. Restriction and modification in *Bacillus subtilis*: Sequence specificities of restriction/modification systems BsuM, BsuE, and BsuF. Journal of Bacteriology. 156:800-808.

Kost C. et al., 2012. PLOS One. Vol. 7, Issue 7. E41349.

Moscoso M et al., 2017. Protective efficacy of a D-alanine auxotroph *Staphylococcus aureus* as a vaccine candidate against staphylococcal disease. 27th ECCMID, Apr. 22, 2017, Vienna, Austria.

Pucci M. J. et al., 1992. J of Bacteriology. p. 336-342.

Thompson R et al., 1998. Pathogenicity and immunogenicity of a *Listeria monocytogenes* strain that requires D-alanine for growth. Infection and Immunity 66:3552-3561.

---

What is claimed is:

1. A recombinant *Staphylococcus* bacterium comprising:
    two inactivated alanine racemase genes (alr1 and alr2); and
    an inactivated D-alanine aminotransferase gene (dat),
wherein the *Staphylococcus* bacterium is *Staphylococcus epidermidis* (*S. epidermidis*), and subspecies thereof, and wherein the *Staphylococcus* bacterium is dependent on D-alanine for growth.

2. The recombinant *Staphylococcus* bacterium of claim 1, wherein the *Staphylococcus* bacterium further comprises one or more additional mutations.

3. The recombinant *Staphylococcus* bacterium of claim 2 in which the additional mutations comprise inactivated glutamatic acid racemase gene, MurI.

4. The recombinant *Staphylococcus* bacterium of claim 1, wherein the bacterium is transformed with a pUBTR114-based vector.

5. The recombinant *Staphylococcus* bacterium of claim 4, wherein the pUBTR114-based vector is pUBTR119*-Sal-GFP.

6. A method of making a recombinant *Staphylococcus* bacterium comprising:
    (i) transforming a plasmid comprising D-alanine aminotransferase (dat) knockout into competent cells of a *Staphylococcus* strain, wherein the *Staphylococcus* strain comprises inactive alanine racemase genes alr1 and alr2 (SEΔalr1Δalr2);
    (ii) detecting the presence of the knockout plasmid in transformed cells;
    (iii) incubating the transformed cells identified in step (ii);
    (iv) purifying isolated colonies; and
    (v) testing the isolated colonies for D-alanine auxotrophy,
wherein the recombinant *Staphylococcus* bacterium is *Staphylococcus epidermidis* (*S. epidermis*), and subspecies thereof.

7. The method of claim 6, wherein the presence of the knockout plasmid in the transformants is detected using Polymerase Chain Reaction (PCR).

8. The method of claim 6, further comprising transforming the recombinant *Staphylococcus* bacterium with a pUBTR114-based vector.

9. The method of claim 8, wherein the pUBTR114-based vector is pUBTR119*-Sal-GFP.

10. A recombinant *Staphylococcus* bacterium produced by the method of claim 6, wherein the recombinant *Staphylococcus* bacterium is *Staphylococcus epidermidis* (*S. epidermis*), and subspecies thereof.

11. A kit comprising the recombinant *Staphylococcus* bacterium of claim 1 or claim 10.

12. The kit of claim 11, further comprising a pUBTR114-based vector.

* * * * *

SEQUENCE LISTING

```
<160> NUMBER OF SEQ ID NOS: 12

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atgcgaattc atgagcgata cttatttgaa tc                                   32

<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctatgcgatt gaatatactt ttccttagca tcctcttcat taac                      44

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gttaatgaag aggatgctaa ggaaaagtat attcaatcgc atag                      44

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agctgtcgac agcagcatac caatgtcaat c                                    31

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 5
catacgaaga tcgaggctac                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtaccaactt gtccgtcttg                                                  20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttgatttaga caattggaag ag                                               22

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aagtacagtc ggcattatct c                                                21

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tttacatatg attcagaaac gtaagcggac agtttcg                               37

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tttttcttgg aattgtgctg cctgcaggtt agtgatggtg                            40

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
acgtctcgag ctgatatttt tgactaaacc aaatg                                    35
```

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 12

```
ctgacctgca ggagatgatc cgctactaac gac                                      33
```